(12) United States Patent
Oberreit

(10) Patent No.: US 10,388,502 B2
(45) Date of Patent: Aug. 20, 2019

(54) CHARGE CONDITIONER TECHNOLOGY

(71) Applicant: Derek Oberreit, Roseville, MN (US)

(72) Inventor: Derek Oberreit, Roseville, MN (US)

( * ) Notice: Subject to any disclaimer, the term of this patent is extended or adjusted under 35 U.S.C. 154(b) by 0 days.

(21) Appl. No.: 15/932,767

(22) Filed: Apr. 23, 2018

(65) Prior Publication Data

US 2018/0308675 A1    Oct. 25, 2018

Related U.S. Application Data

(60) Provisional application No. 62/488,361, filed on Apr. 21, 2017.

(51) Int. Cl.
| | |
|---|---|
| *B01J 19/12* | (2006.01) |
| *G01N 15/02* | (2006.01) |
| *H01J 49/04* | (2006.01) |
| *H01J 49/14* | (2006.01) |
| *G21K 5/10* | (2006.01) |
| *H05F 3/06* | (2006.01) |
| *G01N 15/00* | (2006.01) |
| *G01N 15/06* | (2006.01) |

(52) U.S. Cl.
CPC ......... *H01J 49/0445* (2013.01); *B01J 19/125* (2013.01); *G21K 5/10* (2013.01); *H01J 49/145* (2013.01); *H05F 3/06* (2013.01); *G01N 15/0656* (2013.01); *G01N 2015/0046* (2013.01)

(58) Field of Classification Search
CPC .... H01J 49/0445; H01J 49/145; B01J 19/125; G01N 15/02
See application file for complete search history.

*Primary Examiner* — Nicole M Ippolito
*Assistant Examiner* — Hanway Chang
(74) *Attorney, Agent, or Firm* — Skinner and Associates; Joel Skinner

(57) ABSTRACT

An aerosol charge conditioner includes a source of ionizing radiation, an ionization region, and a conduit transporting an aerosol sample through the ionization region. The conduit is constructed and arranged to control irradiation of the aerosol sample. The conduit includes an inlet conduit communicatively connected to an outlet conduit. The inlet conduit has a first diameter and a distal end disposed in the ionization region. The outlet conduit has a second diameter which is greater than the first diameter of the inlet conduit and a proximal end disposed in the ionization region. A secondary gas supply is communicatively connected to the ionization region. A method for controlled ionization of aerosol particles using radiation as a source is also disclosed.

20 Claims, 8 Drawing Sheets

FIG. 1

CHARGE CONDITIONER TECHNOLOGY

CROSS-REFERENCE TO RELATED APPLICATIONS, IF ANY

This application claims the benefit under 35 U.S.C. § 119(e) of co-pending U.S. Provisional Patent Application Ser. No. 62/488,361, filed Apr. 21, 2017, which is hereby incorporated by reference.

37 C.F.R. § 1.71(E) AUTHORIZATION

A portion of the disclosure of this patent document contains material which is subject to copyright protection. The copyright owner has no objection to the facsimile reproduction by anyone of the patent document or the patent disclosure, as it appears in the US Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to aerosol particle charge conditioning. Particularly, the invention relates to aerosol particle charge conditioning using a source of ionizing radiation. The invention most particularly relates to an aerosol charge conditioner to be used to achieve a steady state bipolar charge distribution on aerosol particles where the exposure of the aerosol to ionization radiation dose is controlled.

2. Background Information

Aerosol particles in the presence of gaseous ions undergo ionization and neutralization through particle-ion collisions. Given sufficient time and bipolar ion concentration, the charge distribution on the aerosol particles will reach a well defined steady state, which is dependent on the particle size and is generally assumed to be independent of particle material and ion composition. Conditioning an aerosol to the steady state bipolar charge distribution is required for accurate quantification of particle concentrations measured using electrostatic based analytical methods.

Conditioning the aerosol to the steady state bipolar change distribution has historically used either radiation sources (radioactive material, soft x-ray, ultraviolet light) that ionize air molecules directly, or a combination of positive and negative corona sources that generate unipolar gas ions through collisions with high energy electrons within the corona plasma. Radioactive sources are not ideal due to regulatory requirements as well as a decay in the total radiative power over time. Soft x-ray emitters are suitable sources for ionizing radiation, however, in practical application the x-ray energy is sufficiently high to produce particles through radiolytically induced reactions between gas molecules or disassociation of metastable aerosol particles. The effect of radiolytically induced artifacts can be mitigated through control of the ionization energy (either the x-ray power or through the use of an attenuator), by controlling the exposure time of the aerosol particles and particle precursors to the soft x-rays, and/or by controlling the ionized gas species exposed to the ionization energy.

In summary, radioactive and corona sources are difficult to respectively transport and maintain. Soft X-Ray has the advantage of low maintenance and limited restriction of use. However, direct exposure of some gases to soft x-ray radiation can create electrolytically generated aerosol particles which may interfere with the measurement. Previous devices using soft x-ray ionization have utilized an attenuation window to sufficiently reduce the x-ray energy to minimize the generation of particles. While this method is effective for general charge conditioning, it does not allow for controlled charging ion creation (chemical ionization).

US Patent Application Publication No. 2006/0108537 published May 25, 2006, by Okuyama, et al. discloses aerosol particle charging equipment.

U.S. Pat. No. 7,796,727, issued Sep. 14, 2010 to Kaufman discloses an aerosol charge conditioner.

Bangwoo Han, Manabu Shimada, Mansoo Choi, & Kikuo Olcuyama (2003), Unipolar Charging of Nanosized Aerosol Particle Using Soft X-ray Photoionization, Aerosol Science and Technology, 37:4, 330-341 disclose a unipolar charging device based on soft X-ray photoionization. (copy attached).

Existing technology in this field is believed to have significant limitations and shortcomings. For this and other reasons, a need exists for the present invention.

All US patents and patent applications, and all other published documents mentioned anywhere in this application are incorporated by reference in their entirety.

BRIEF SUMMARY OF THE INVENTION

The invention provides a soft X-ray charge conditioner system, apparatus, and method which are practical, reliable, accurate and efficient, and which are believed to fulfill the need and to constitute an improvement over the background technology.

Aerosol charge conditioning applies a known charge distribution to aerosol particles which facilitates quantification of aerosol concentration following electrical measurement methods (electrostatic classification, electrometer measurement).

The invention provides an aerosol charge conditioning apparatus, comprising:

a. a source of ionizing radiation;
b. an ionization region;
c. a conduit transporting an aerosol sample through the ionization region; the conduit being constructed and arranged to control irradiation of the aerosol sample, the conduit including an inlet conduit communicatively connected to an outlet conduit, the inlet conduit having a first diameter and a distal end disposed in the ionization region, and the outlet conduit having a second diameter which is greater than the first diameter of the inlet conduit and a proximal end disposed in the ionization region; and
d. a secondary gas supply communicatively connected to the ionization region.

In one embodiment, the inlet conduit distal end is disposed within the proximal end of the outlet conduit, and wherein there is an annular gap between the inlet conduit and the outlet conduit, whereby the secondary gas enters the outlet conduit through the annular gap sheathing aerosol flowing in the conduit, and whereby the secondary gas is irradiated in the ionization region and aerosol sample is shielded from direct exposure from the source of ionizing radiation. In another embodiment, wherein the inlet conduit distal end is disposed near the proximal end of outlet conduit, the inlet conduit distal end and the outlet conduit proximal end being separated by a gap, aerosol flowing across the gap from the inlet conduit to the outlet conduit, the gap being directly exposed to the source of ionizing radiation, and whereby the secondary gas enters the outlet conduit through the annular gap.

The invention relates to an aerosol charge conditioning device that allows for controlled exposure of ionizing radiation to species within an aerosol sample flowing within a conduit. In one aspect, the aerosol is directly exposed to ionizing radiation where the dose is controlled by modifying the flowrate of the aerosol, the area of a transmissive section of the conduit, and the conduit diameter. In this aspect, a secondary purge gas may be used to mitigate exfiltration of particles and gaseous particle precursors from the flow conduit into an adjacent region that is exposed to the ionizing radiation. In another aspect, the aerosol is fully shielded from direct ionizing radiation and charge conditioning is accomplished by a secondary gas that is exposed to the ionizing radiation where the resulting bipolar gas ions are advectively transported to and combined with the aerosol flowing in the conduit. In this aspect, the ionizing species can be deliberately chosen to facilitate chemical ionization.

In another aspect, the invention provides a charge conditioner including a soft X-ray source, an ionization housing, an ionizing gas inlet, an aerosol inlet, and an aerosol outlet.

In yet another aspect, the invention provides a method for controlled ionization of aerosol particles using soft x-ray radiation as a source. Gas of a controlled composition is introduced into the ionization housing where it is exposed to soft x-ray radiation. The ionized gas molecules are then introduced as a sheath flow around the aerosol stream where the aerosol particles are then charged from collisions with ions diffusing through the aerosol stream. The sheathing flow may be extracted at the exit of the charge conditioner.

The aspects, features, advantages, benefits and objects of the invention will become clear to those skilled in the art by reference to the following description, claims and drawings.

BRIEF DESCRIPTION OF THE SEVERAL VIEWS OF THE DRAWING

FIG. 1 is a diagrammatic representation of one embodiment of a charge conditioner system, apparatus and method of the present invention.

DETAILED DESCRIPTION

Figure 1:
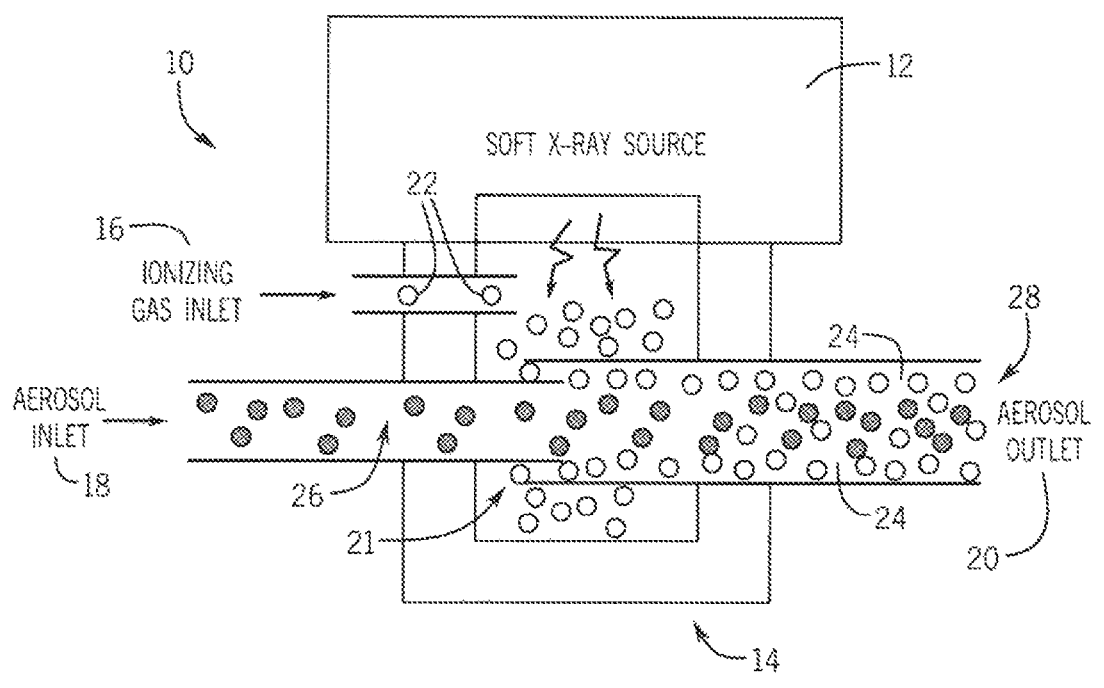
Figure 2:
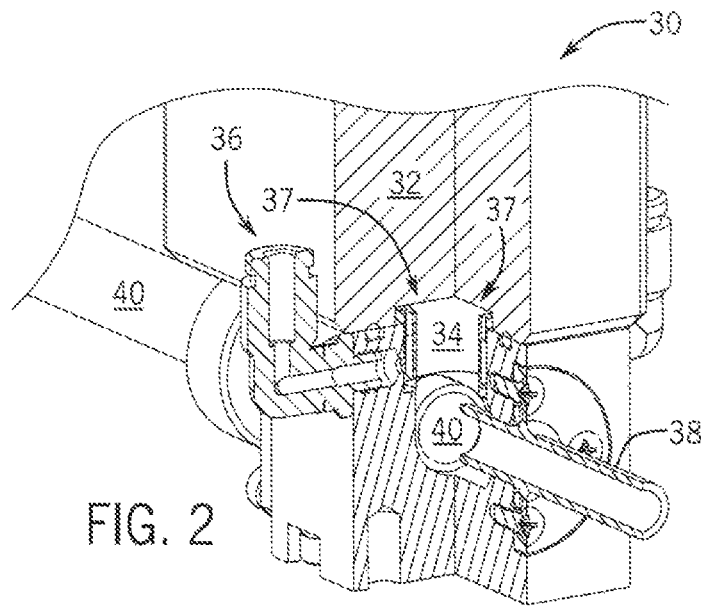
FIG. 2 is a perspective view, partially in section, of another embodiment of the charge conditioner apparatus of the invention.

FIG. 1 is a diagram of an embodiment of the system, apparatus and method of the present invention. This embodiment of the invention utilizes indirect radiation, particularly soft X-ray radiation. The system does not expose aerosol to ionization energy. It permits prescribed chemical ionization. A sheathed configuration reduces diffusional losses.

The charge conditioner 10 basically comprises a radiation source 12, an ionization housing 14, an ionizing gas inlet 16, an aerosol inlet 18, and an aerosol outlet 20. Ionizing gas of a controlled composition is introduced, via inlet 16, into the ionization housing 14 where it is exposed to soft x-ray radiation generated by the source 12. The ionized gas molecules 22 are then introduced, via inlet 18, as a sheath flow 24 around an aerosol stream 26 (formed of a sample input at the proximal end of inlet 18) where the aerosol particles 26 are then charged from collisions with ions 22 diffusing through the aerosol stream 26. The sheathing flow 24 may be extracted and removed from the sample stream 26 at the exit 28 of the charge conditioner 10.

The radiation source 12 is preferably a soft X ray emitter. Alternatively, it may be a radioactive isotope or an ultraviolet light emitter. The ionization housing 14 has a predetermined volume and configuration, and is disposed below the radiation source 12. The ionizing gas inlet 16 is a conduit, shown disposed at the top of the housing 14 proximate the radiation source, in this embodiment. The ionizing gas may be conditioned to remove particle precursors. It may also be formulated to facilitate chemical ionization. The aerosol inlet 18 is preferably a conduit of a predetermined diameter entering the housing 14 at a first end thereof, and extending a predetermined distance thereinto. The inlet conduit 18 is constructed of a material that blocks radiation from the radiation source 12. The aerosol outlet 20 is a conduit having a diameter larger than that of the aerosol inlet 18. The outlet conduit 20 extends over the distal end of the inlet conduit 18 and then exits the housing 14. The outlet conduit 20 is also constructed of a material that is impervious to radiation from source 12. Ionizing gas molecules 22 enter a longitudinal, annular gap 21 between the inlet and outlet conduits 18 and 20, respectively, with in the ionization housing 14. Together, the aerosol inlet and outlet 18 and 20 define a conduit which advectively transports the aerosol sample 26. This conduit arrangement permits controlled exposure of the aerosol 26 to ionizing radiation. However, the aerosol is shielded from direct exposure to the radiation source 12 by the respective wall of the conduit 18/20.

Figure 3:
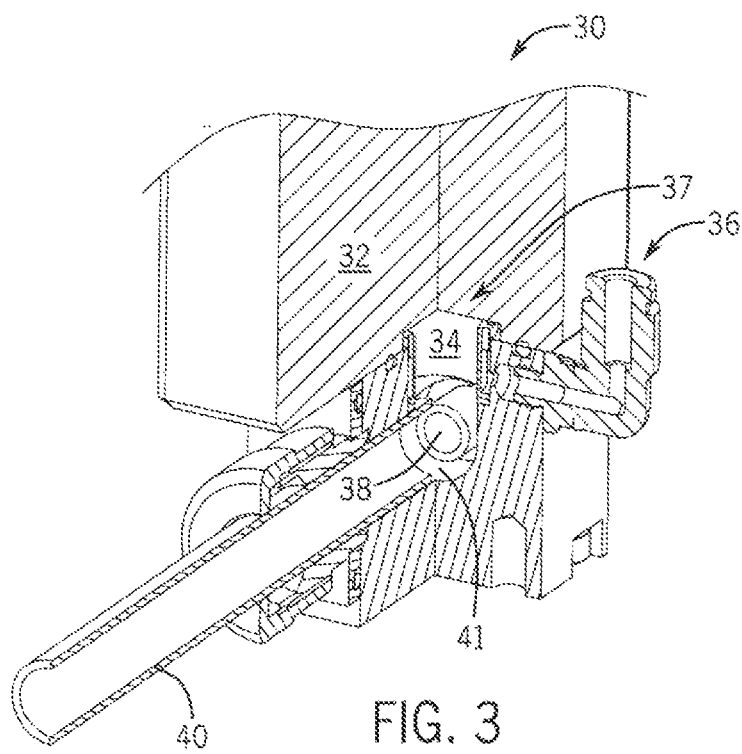
FIG. 3 is another perspective view, partially in section, of the charge conditioner apparatus of FIG. 2.
Figure 5:
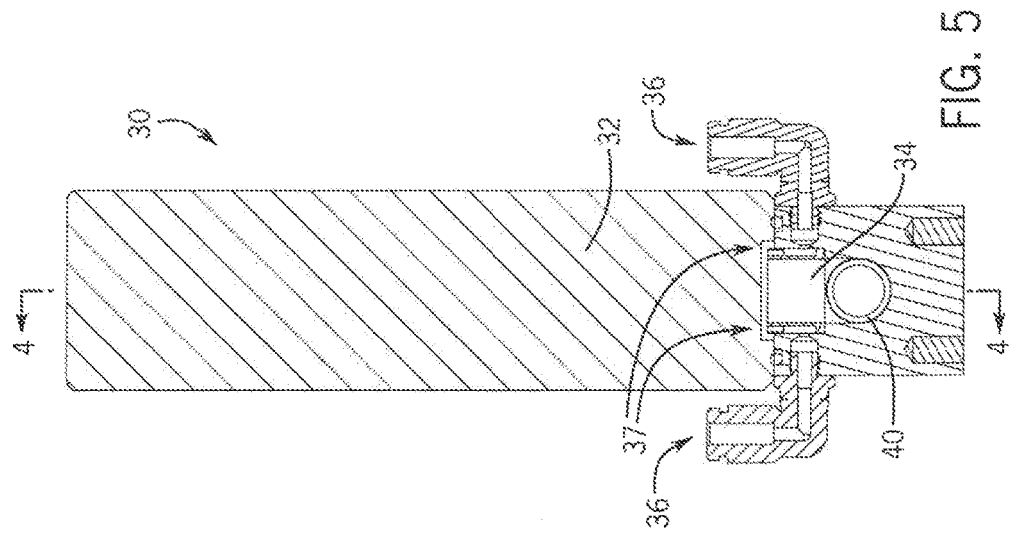
FIG. 5 is a crossectional view of the charge conditioner apparatus taken along line 5-5 of FIG. 4.
Figure 4:
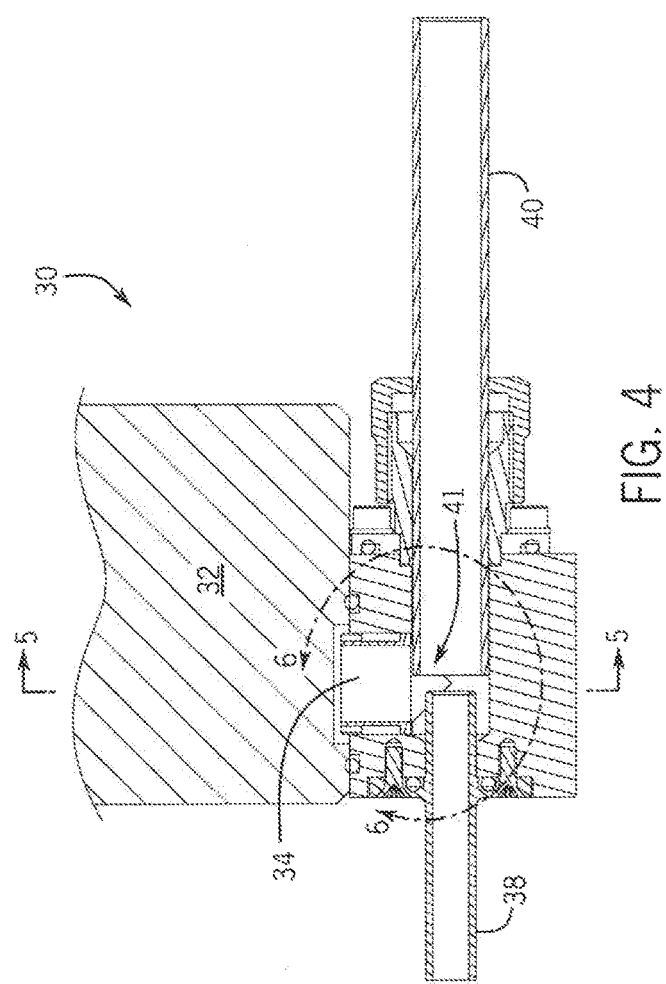
FIG. 4 is a side or elevation view, in section, of the charge conditioner apparatus of FIGS. 2 and 3, where the aerosol conduit is configured for direct exposure to ionization energy from a radiation source.
Figure 6:
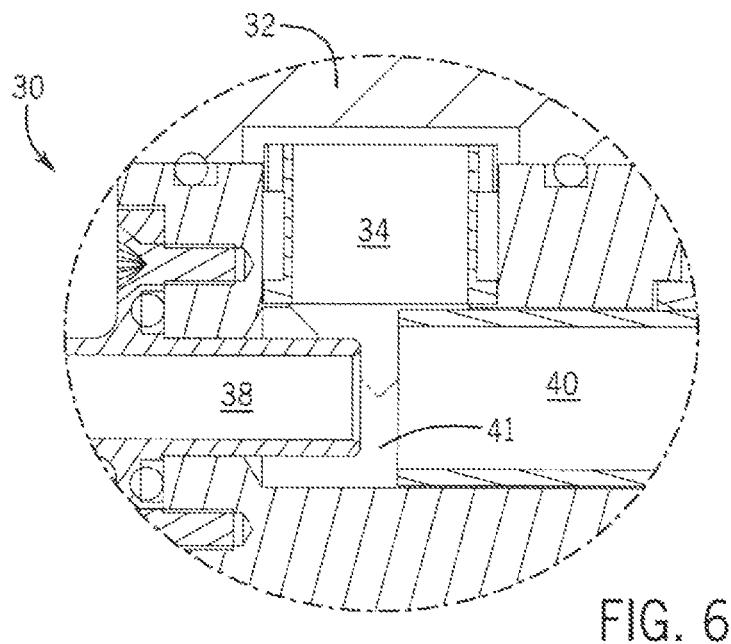
FIG. 6 is a detailed view of the charge conditioner apparatus taken at area "6" of FIG. 5.

FIGS. 2-6 shows another embodiment of the system, apparatus and method of the present invention. This embodiment utilizes direct ionization energy. FIGS. 2 and 3 are isometric views, at the elevation level, of the inlet and outlet, respectively, of the apparatus. FIGS. 4 and 5 are elevation views, in section, of the side and ends of the apparatus, respectively. And FIG. 6 is a detailed view of the direct ionization chamber.

The aerosol charge conditioner apparatus 30 of this embodiment of the invention also comprises a radiation source 32, an ionization housing 34, an ionizing gas inlet 36, and an aerosol outlet 40. The apparatus 30 further comprises one or more secondary gas inlets 36.

Ionizing gas of a controlled composition is introduced, via inlet 16, into the ionization housing 14 where it is exposed to soft x-ray radiation generated by the source 12. The ionized gas molecules 22 are then introduced, via inlet 18, as a sheath flow 24 around an aerosol stream 26 (formed of a sample input at the proximal end of inlet 18) where the aerosol particles 26 are then charged from collisions with ions 22 diffusing through the aerosol stream 26. The sheathing flow 24 may be extracted and removed from the sample stream 26 at the exit 28 of the charge conditioner 10.

The radiation source 32 is also preferably a soft X ray emitter. Alternatively, it may be a radioactive isotope or an ultraviolet light emitter. The ionization housing 34 has a predetermined volume and configuration, and is disposed below the radiation source 32. The secondary gas inlets 36 are preferably a pair of conduits, shown disposed entering the ionizing chamber 34 above the aerosol conduits 38 and 40, in this embodiment. The aerosol inlet 38 is preferably a conduit of a predetermined diameter entering the housing 34 at a first end thereof, and extending a predetermined distance thereinto. The inlet conduit 38 is constructed of a material that blocks radiation from the radiation source 32. The aerosol outlet 40 is a conduit having a diameter larger than that of the aerosol inlet 38. In this embodiment, the outlet conduit 40 does not extend over the distal end of the inlet conduit 18, but instead is separated from it a predetermined distance forming a gap 41. the outlet conduit 40 then exits the housing 34. The outlet conduit 40 is also constructed of a material that is impervious to radiation from source 32. Secondary gas is input to the ionization housing 34 via the secondary gas conduits 36. Together, the aerosol inlet and outlet 38 and 40 define a conduit which advectively transports the aerosol sample. This conduit arrangement also permits controlled exposure of the aerosol to ionizing radiation. In this embodiment, the aerosol is directly exposed to the radiation source 32 by the geometry of the gap.

In use, an aerosol sample is adjectively transported to the flow conduit 38. The aerosol is then exposed to ionizing radiation at the gap 41. The exposure dose is controlled by adjusting the gap 41 between the inlet conduit 38 and the outlet conduit 40. This gap 41 is preferably adjustable, most preferably by adjusting the axial position of the outlet conduit 41. A secondary gas of controlled composition is introduced via inlets 36. The secondary gas is evenly distributed by manifold 37 where it is introduced proximally to the radiation source 32 and then advectively transported to the gap 41 to then combine with the aerosol sample flow through conduits 38 and 40.

Figure 7:
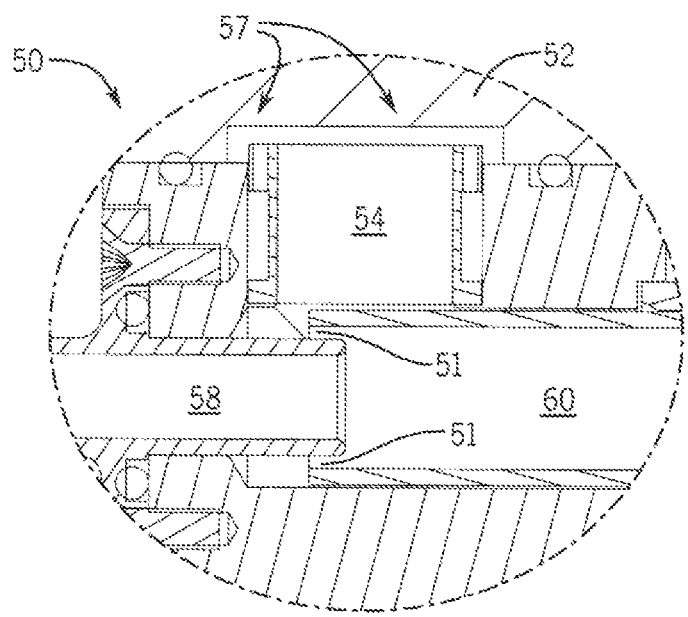
FIG. 7 is a detailed view of another embodiment of the charge conditioner apparatus where the conduit is configured for indirect ionization by a secondary gas.

FIG. 7 discloses a further alternative embodiment of the aerosol conditioning apparatus of the invention. This embodiment involves a modified configuration of the base apparatus disclosed with respect to FIGS. 2-6. In this embodiment of the apparatus 50, the aerosol sample is fully shielded from the ionizing radiation. Gas of a controlled composition is introduced via a gas supply line not shown into a manifold 57 and then into the ionization housing 54 where it is exposed to ionizing radiation from source 52. The ionized gas molecules are then introduced as a sheathing flow via annular aperture 51 around the aerosol stream flowing through inlet 58 and outlet 60 where the ions and aerosol particles mix and transfer charge through ion-particle collisions.

Figure 8:
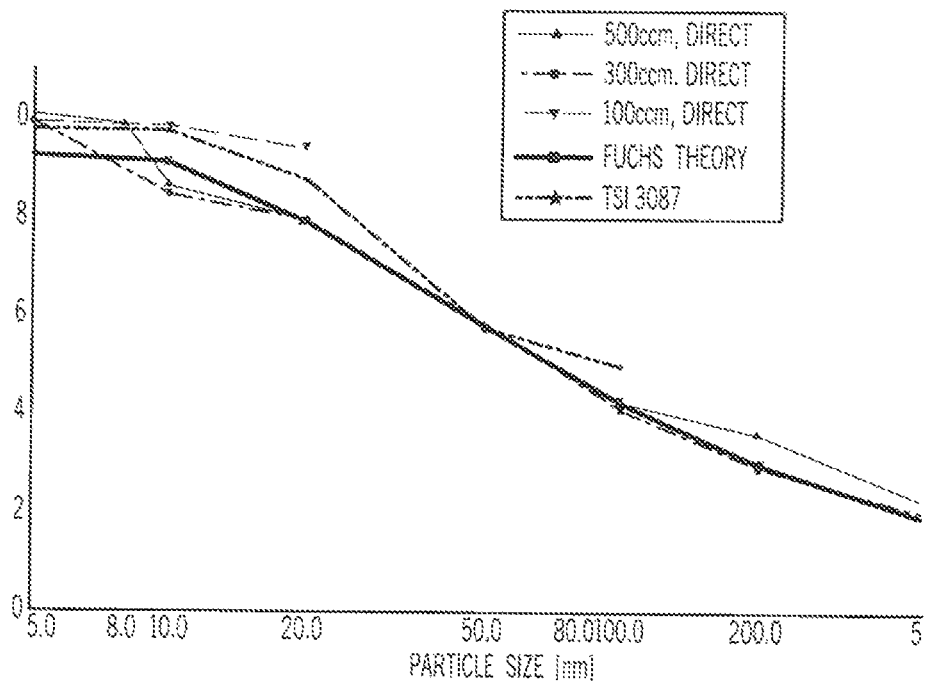
FIG. 8 is a graph which shows the charge conditioning efficiency compared to theory utilizing the direct exposure to ionization energy from a radiation source via the charge conditioner apparatus of FIGS. 2-6.

FIG. 8 is a graph which shows the charge conditioning efficiency compared to theory utilizing the direct exposure to ionization energy from a radiation source via the charge conditioner apparatus of FIGS. 2-6.

Figure 9:
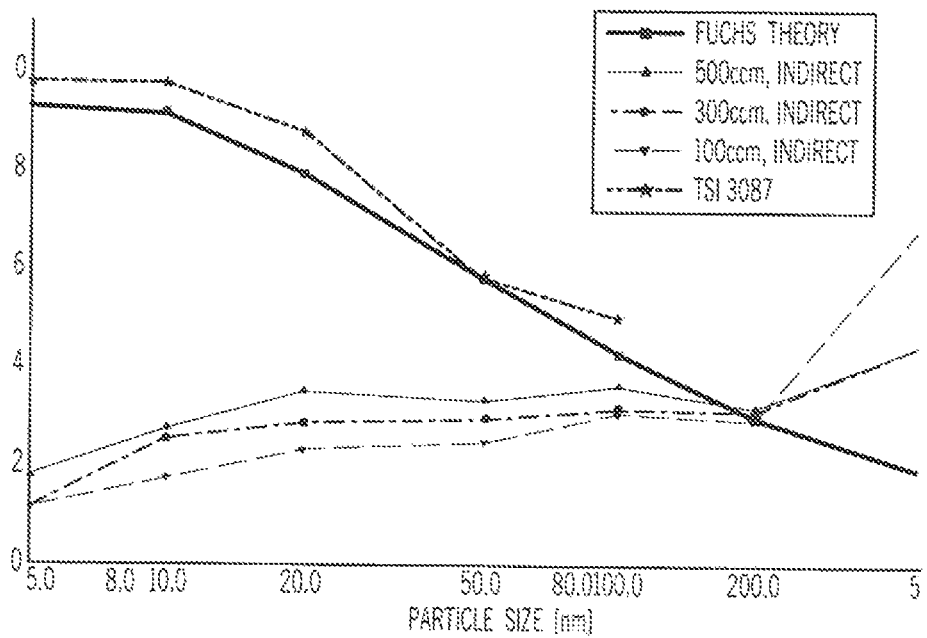
FIG. 9 is a graph showing the charge conditioning efficiency compared to theory utilizing the indirect exposure to ionization energy from a radiation source via the charge conditioner apparatus of FIG. 7.

FIG. 9 is a graph showing the charge conditioning efficiency compared to theory utilizing the indirect exposure to ionization energy from a radiation source via the charge conditioner apparatus of FIG. 7.

Figure 10:
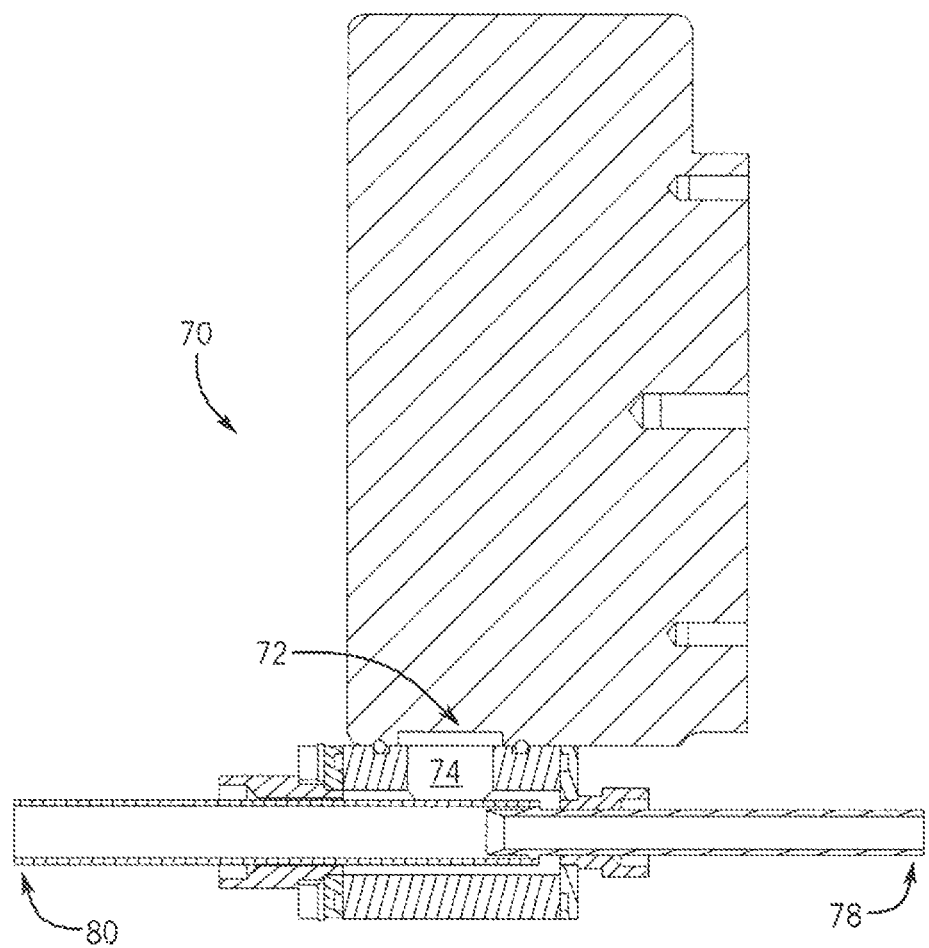
FIG. 10 is a side elevation view, in section, of a further embodiment of the charge conditioner apparatus of the invention.
Figure 11:
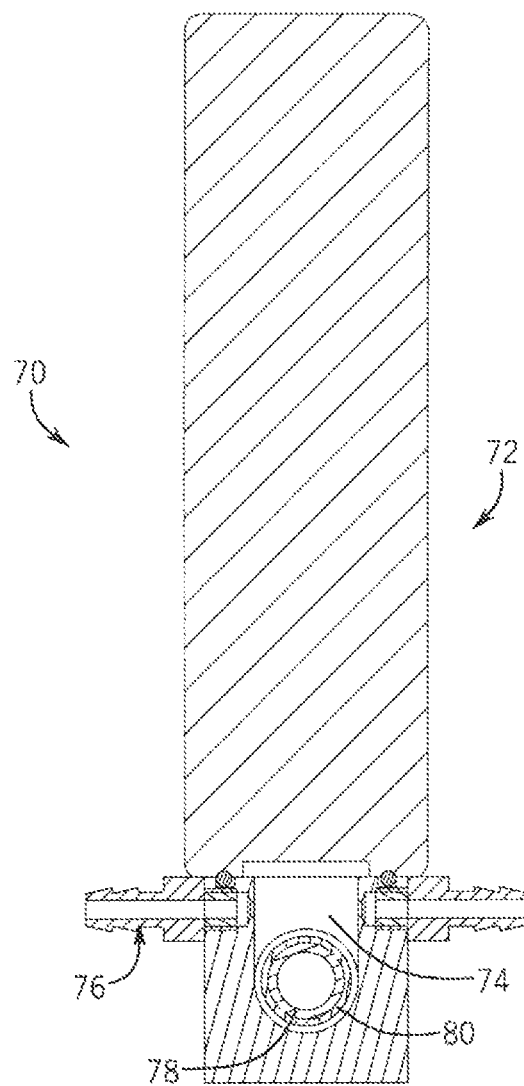
FIG. 11 is an end elevation view, in section, of the apparatus of FIG. 10.
Figure 12:
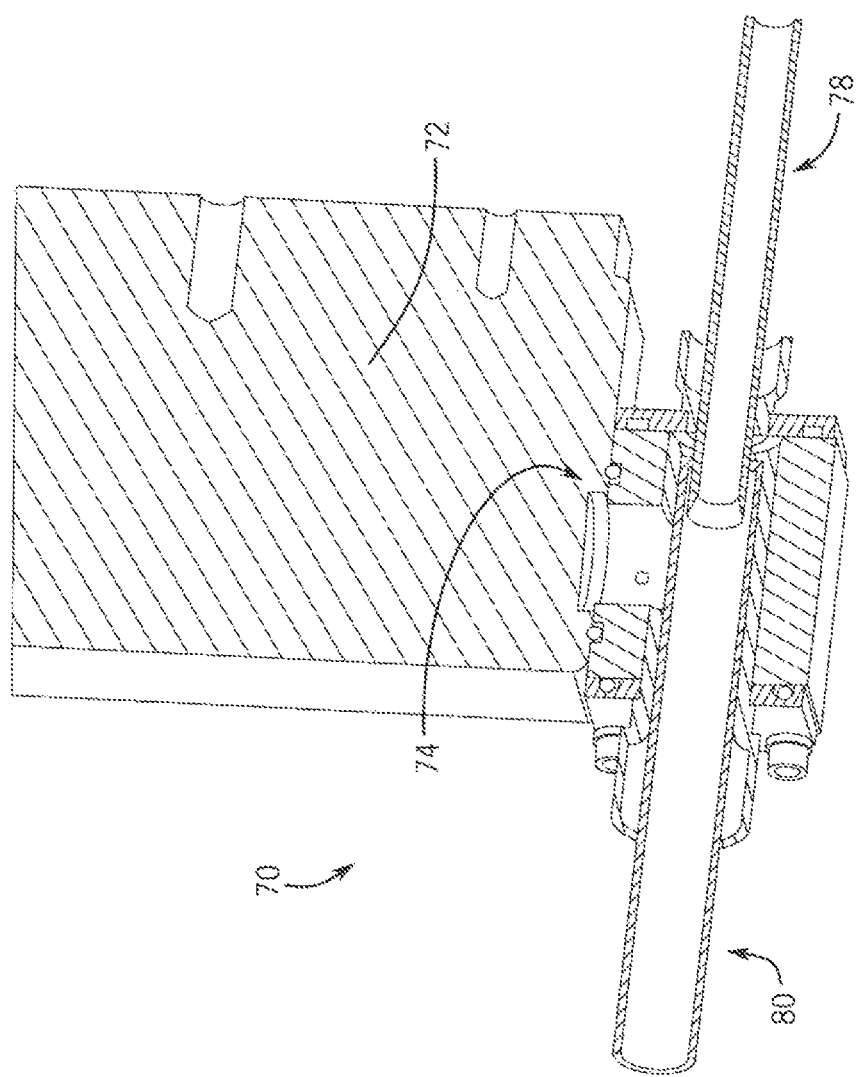
FIG. 12 is an isometric view, partially in section, of the charge conditioner apparatus of FIGS. 10 and 11.

FIGS. 10-12 shows yet another embodiment of the charge conditioning system of the present invention. This embodiment utilizes indirect ionization, preferably soft X ray, disclosed with respect to the diagrammatic illustration of FIG. 1 and the detailed portion shown in FIG. 7. FIG. 10 is a side elevation view, in section, of the charge conditioner 70. FIG. 11 is an end elevation view, in section. And FIG. 12 is an isometric view, partially in section, of the charge conditioner apparatus 70. The charge conditioner 70 comprises a soft X-ray source 72, an ionization housing 74, an ionizing gas inlet 76, an aerosol inlet 78, and an aerosol outlet 80. Gas of a controlled composition is introduced into the ionization housing 74 where it is exposed to soft x-ray radiation. The ionized gas molecules are then introduced as a sheath flow around the aerosol stream where the aerosol particles are then charged from collisions with ions diffusing through the aerosol stream. The sheathing flow may be extracted at the exit of the charge conditioner.

It is within the purview of the invention that one or more perforations in the inlet or outlet aerosol conduits could provide a entry of irradiated or non irradiated secondary gas, and/or could provide direct exposure to aerosol gas flowing in such conduit to the radiation source. It is also within the purview of the invention that the secondary gas be composed of the gas within the aerosol sample.

The embodiments above are chosen, described and illustrated so that persons skilled in the art will be able to understand the invention and the manner and process of making and using it. The descriptions and the accompanying drawings should be interpreted in the illustrative and not the exhaustive or limited sense. The invention is not intended to be limited to the exact forms disclosed. While the application attempts to disclose all of the embodiments of the invention that are reasonably foreseeable, there may be unforeseeable insubstantial modifications that remain as equivalents. It should be understood by persons skilled in the art that there may be other embodiments than those disclosed which fall within the scope of the invention as defined by the claims. Where a claim, if any, is expressed as a means or step for performing a specified function it is intended that such claim be construed to cover the corresponding structure, material, or acts described in the specification and equivalents thereof, including both structural equivalents and equivalent structures, material-based equivalents and equivalent materials, and act-based equivalents and equivalent acts.

The invention claimed is:

1. An aerosol charge conditioning apparatus, comprising:
a source of ionizing radiation;
an ionization region;
a conduit transporting an aerosol sample through the ionization region; the conduit being constructed and arranged to control irradiation of the aerosol sample; and a secondary gas supply communicatively connected to the ionization region.

2. The aerosol charge conditioning apparatus of claim 1, where the source of ionizing radiation is a soft x-ray emitter.

3. The aerosol charge conditioning apparatus of claim 1, where the source of ionizing radiation is a radioactive isotope.

4. The aerosol charge conditioning apparatus of claim 1, where the source of ionizing radiation is an ultraviolet light emitter.

5. The aerosol charge conditioning apparatus of claim 1, wherein the ionization region surrounds at least a portion of the conduit.

6. The aerosol charge conditioning apparatus of claim 1, wherein the conduit comprises an inlet conduit communicatively connected to an outlet conduit.

7. The aerosol charge conditioning apparatus of claim 6, wherein the inlet conduit has a first diameter and a distal end disposed in the ionization region, and wherein the outlet conduit has a second diameter which is greater than the first diameter of the inlet conduit and has a proximal end disposed in the ionization region.

8. The aerosol charge conditioning apparatus of claim 7, wherein the inlet conduit distal end is disposed within the proximal end of the outlet conduit, and wherein there is an annular gap between the inlet conduit and the outlet conduit, whereby the secondary gas enters the outlet conduit through the annular gap sheathing aerosol flowing in the conduit, and whereby the secondary gas is irradiated in the ionization region and aerosol sample is shielded from direct exposure from the source of ionizing radiation.

9. The aerosol charge conditioning apparatus of claim 8 where the secondary gas is laminarily introduced through the annular gap to the aerosol sample flow.

10. The aerosol charge conditioning apparatus of claim 9 where the annular flow secondary gas is removed from the aerosol sample flow at a predetermined time.

11. The aerosol charge conditioning apparatus of claim 8 where the secondary gas is turbulently introduced through the annular gap to the aerosol sample flow.

12. The aerosol charge conditioning apparatus of claim 7, wherein the inlet conduit distal end is disposed near the proximal end of outlet conduit, the inlet conduit distal end and the outlet conduit proximal end being separated by a gap, aerosol flowing across the gap from the inlet conduit to the outlet conduit, the gap being directly exposed to the source of ionizing radiation, and whereby the secondary gas enters the outlet conduit through the annular gap.

13. The aerosol charge conditioning apparatus of claim 12, wherein the gap is adjustable.

14. The aerosol charge conditioning apparatus of claim 1, wherein the conduit is constructed of material that blocks radiation.

15. The aerosol charge conditioning apparatus of claim 1, wherein the conduit advectively transports the aerosol through the ionization region.

16. The aerosol charge conditioning apparatus of claim 1 wherein the secondary gas is introduced to the ionization region via a manifold.

17. The aerosol charge conditioning apparatus of claim 1 where the secondary gas is conditioned to remove particle precursors.

18. The aerosol charge conditioning apparatus of claim 1 where the secondary gas contains molecules which facilitate chemical ionization.

19. An aerosol charge conditioning apparatus, comprising:
  a. a source of ionizing radiation;
  b. an ionization region;
  c. a conduit transporting an aerosol sample through the ionization region; the conduit being constructed and arranged to control irradiation of the aerosol sample, the conduit including an inlet conduit communicatively connected to an outlet conduit, the inlet conduit having a first diameter and a distal end disposed in the ionization region, and the outlet conduit having a second diameter which is greater than the first diameter of the inlet conduit and a proximal end disposed in the ionization region; and
  d. a secondary gas supply communicatively connected to the ionization region.

20. An aerosol charge conditioning apparatus, comprising:
  a. a source of ionizing radiation;
  b. an ionization region;
  c. a conduit transporting an aerosol sample through the ionization region; the conduit being constructed and arranged to control irradiation of the aerosol sample, the conduit including:
    i. an inlet conduit communicatively connected to
    ii. an outlet conduit, whereby
    iii. wherein the inlet conduit has a first diameter and a distal end disposed in the ionization region, and the outlet conduit has a second diameter which is greater than the first diameter of the inlet conduit and a proximal end disposed in the ionization region,
    iv. wherein the inlet conduit distal end is disposed near the proximal end of outlet conduit,
    v. wherein the inlet conduit distal end and the outlet conduit proximal end are separated by a gap,
    vi. whereby aerosol flows across the gap from the inlet conduit to the outlet conduit, the gap being directly exposed to the source of ionizing radiation, and
    vii. whereby the secondary gas enters the outlet conduit through the annular gap; and
  d. a secondary gas supply communicatively connected to the ionization region.

* * * * *